(12) United States Patent
Gassner et al.

(10) Patent No.: US 11,974,758 B2
(45) Date of Patent: May 7, 2024

(54) ORIENTATION APPARATUS WITH FEEDBACK

(71) Applicant: Aesculap AG, Tuttlingen (DE)

(72) Inventors: Stefan Gassner, Immendingen-Hattingen (DE); Jana Schuele, Kreenheinstetten (DE)

(73) Assignee: Aesculap AG, Tuttlingen (DE)

( * ) Notice: Subject to any disclaimer, the term of this patent is extended or adjusted under 35 U.S.C. 154(b) by 353 days.

(21) Appl. No.: 17/610,540

(22) PCT Filed: Apr. 23, 2020

(86) PCT No.: PCT/EP2020/061292
§ 371 (c)(1),
(2) Date: Nov. 11, 2021

(87) PCT Pub. No.: WO2020/229129
PCT Pub. Date: Nov. 19, 2020

(65) Prior Publication Data
US 2022/0211389 A1    Jul. 7, 2022

(30) Foreign Application Priority Data
May 16, 2019 (DE) ...................... 10 2019 112 897.8

(51) Int. Cl.
*A61B 17/15* (2006.01)
(52) U.S. Cl.
CPC .................. *A61B 17/157* (2013.01)
(58) Field of Classification Search
CPC ................................... A61B 17/157
See application file for complete search history.

(56) References Cited

U.S. PATENT DOCUMENTS

| 5,681,316 A | 10/1997 | DeOrio et al. |
| 2005/0187560 A1 | 8/2005 | Dietzel et al. |
| 2010/0063508 A1 | 3/2010 | Borja et al. |
| 2011/0046685 A1 | 2/2011 | Faure et al. |

(Continued)

FOREIGN PATENT DOCUMENTS

| CA | 2978210 A1 | 9/2016 |
| CN | 102149337 A | 8/2011 |

(Continued)

OTHER PUBLICATIONS

Search Report received in German Application No. 10 2019 112 897.8 dated Jan. 17, 2020, with translation, 13 pages.

(Continued)

*Primary Examiner* — Sameh R Boles
(74) *Attorney, Agent, or Firm* — Christopher A. Rothe; Culhane Meadows PLLC

(57) ABSTRACT

A touch/orientation apparatus having, for orienting a saw template: an adjusting element, a moving element having a profiled indentation, a feeler that is movable relative to the adjusting element, a scale for measuring the height of the adjusting element relative to the moving element, at least one first stop formed on the adjusting element, and at least one second stop formed on the scale or acting as a scale and being provided and adapted to function as a resistance to the first stop. The second stop and/or the first stop resiliently deflects the respective other stop.

10 Claims, 7 Drawing Sheets

(56) References Cited

U.S. PATENT DOCUMENTS

Figure 4:
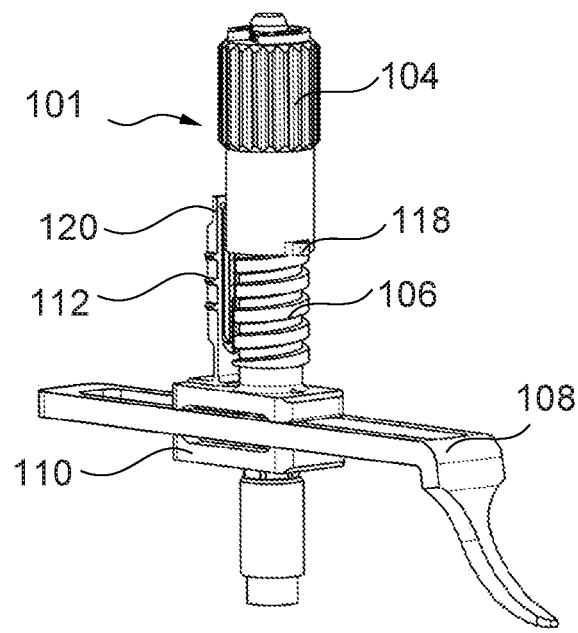

2011/0160735 A1\* 6/2011 Cowan ................... A61B 17/17
                                                        606/87
2013/0158556 A1   6/2013 Jones et al.
2017/0252186 A1   9/2017 Lorio et al.

FOREIGN PATENT DOCUMENTS

| CN | 103002818 A   | 3/2013 |
| CN | 104394805 A   | 3/2015 |
| CN | 107530172 A   | 1/2018 |
| JP | 2012501774 A  | 1/2012 |
| JP | 2018507074 A  | 3/2018 |
| WO | 2010029333 A1 | 3/2010 |
| WO | 2016141274 A1 | 9/2016 |
| WO | 2018169980 A1 | 9/2018 |

OTHER PUBLICATIONS

Search Report received in International Application PCT/EP2020/061292 dated Jul. 9, 2020, with translation, 7 pages.
Written Opinion received in International Application PCT/EP2020/061292 dated Jul. 9, 2020, with translation, 12 pages.
Office Action received in Chinese Application No. 202080029239.5 dated Jun. 26, 2023, with translation, 12 pages.
Office Action received in Japanese Application No. 2021-568440 dated May 27, 2022, with translation, 7 pages.

\* cited by examiner

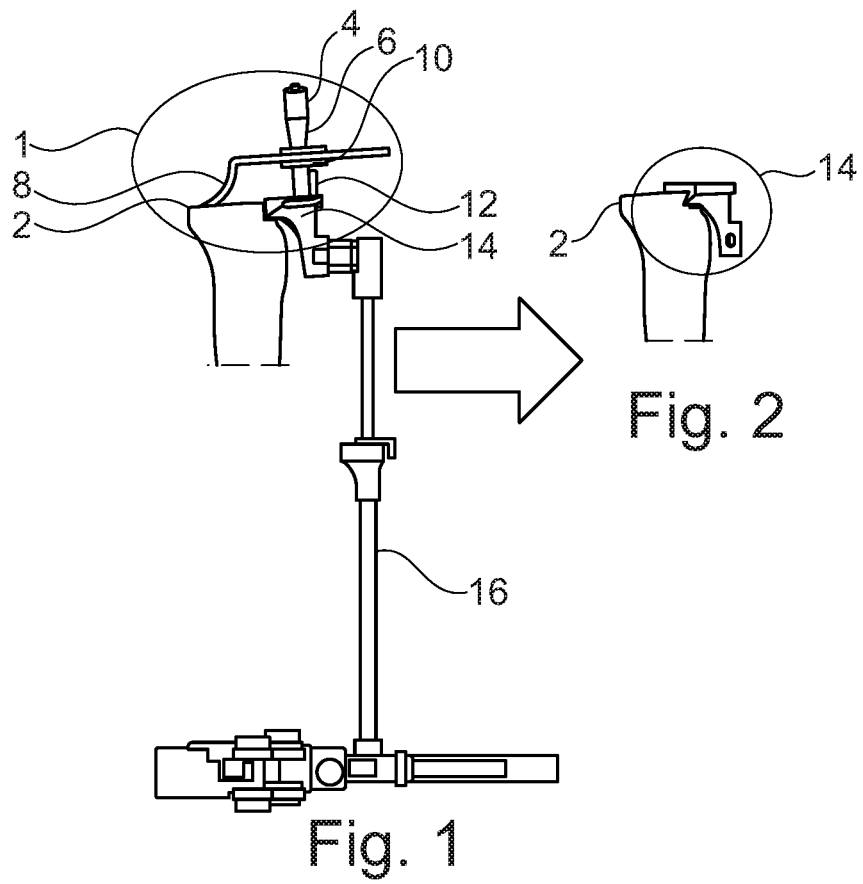
Fig. 2
Fig. 1
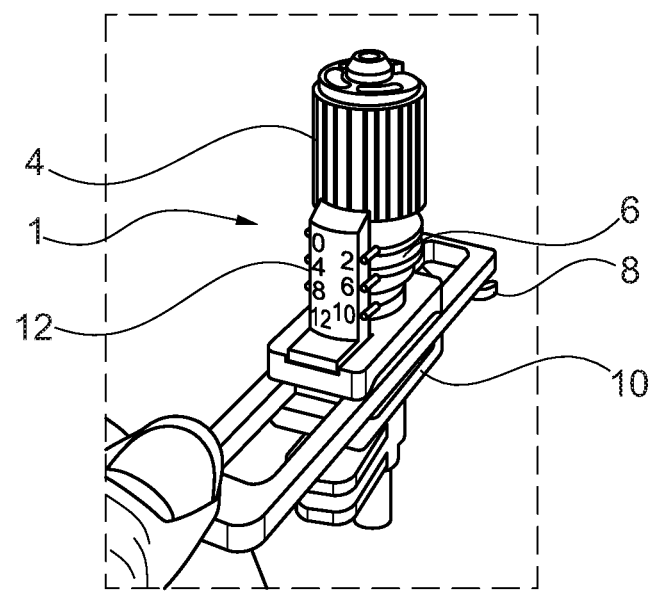
Fig. 3

ORIENTATION APPARATUS WITH FEEDBACK

CROSS-REFERENCE TO RELATED APPLICATIONS

This application is the United States national phase entry of International Application No. PCT/EP2020/061292, filed Apr. 23, 2020, and claims the benefit of priority of German Application No. 10 2019 112 897.8, filed May 16, 2019. The contents of International Application No. PCT/EP2020/061292 and German Application No. 10 2019 112 897.8 are incorporated by reference herein in their entireties.

FIELD

The present invention relates to an apparatus or orientation aid for orienting a saw template or sawing block for removing an area of the tibial plateau during implantation of a knee joint prosthesis (hereinafter also referred to as tibial orientation aid).

BACKGROUND

When implanting, for example, an artificial knee joint, a surgeon has to remove, among other things, the defective head part of the tibial knee joint (tibial plateau, tibial head) with an oscillating bone saw. For this purpose, the surgeon uses an orientation device or orientation aid, which enables him to attach a saw template (also known as a sawing block) to the tibial head at the correct height and angle with respect to the tibia.

At the beginning of an implantation, the template is held to the tibial head by an extramedullary or intramedullary holding apparatus (which has or is the orientation aid). In other words, the holder of the template can be held to the tibial head "extramedullary", i.e. by a holder that is attached externally to the leg or tibia, or "intramedullary", i.e. by a bone nail or intramedullary nail or the like that is inserted into the tibia bone. Once the template is held to the tibia by the extramedullary or intramedullary holding apparatuses, fine adjustment of the relative position and orientation of the template is performed by a stylus (this is the orientation aid and may be part of the holding apparatus). The stylus determines the correct height of the template relative to the tibial head on the bone itself. Once the height is found, the template is screwed to the tibial head via screws and the holding apparatus including the stylus is removed again.

In order to position the artificial tibial component of the artificial joint on the original joint line, the physician has to probe the deepest defect site in the bone using the stylus and then has to set the thickness of the bone piece to be removed using a rotary knob and a scale. The value to be adjusted usually corresponds to the manufacturer-specific implant thickness, thus restoring the original joint line. From a medical point of view, however, it may be necessary to deviate from the original joint line and to move it in a targeted manner towards the body/in the distal direction or away from the body/in the proximal direction.

A knee prosthesis, knee endoprosthesis, artificial knee joint or knee joint prosthesis is an implanted prosthesis (endoprosthesis) that completely or partially replaces the knee joint. The knee prosthesis is mainly used in cases of severe wear and tear of the knee (knee joint arthrosis) and after injuries of the knee as a surgical therapy to restore pain-free mobility and, if necessary, also knee joint stability in cases of ligament instability. Partial or total endoprostheses may be used.

The shin bone (tibia) is one of the two bones of the lower leg, along with the calf bone (fibula). The shin bone is the stronger one of the two bones and is a typical tubular bone. The upper end, the head (caput tibiae), is the strongest part and carries two condyles (condylus medialis and condylus lateralis). In anatomy, the term condyle or ankle refers to the bony part of a joint, which is also called the articular process. In the knee joint, the upper end of the shin bone (tibia) and the lower end of the thigh bone (femur) each bear two condyles. On their upper surface, these have a cartilage-covered articular surface (facies articularis superior), which is separated into two parts by an elevation (eminentia intercondylaris). The elevation runs into two separate small knobs (tuberculum intercondylare mediale and tuberculum intercondylare laterale). It is bounded at the front (ventral) and back (dorsal) by two shallow pits (area intercondylaris anterior and area intercondylaris posterior). The crucial ligaments and the retinacula of the menisci are attached here. The entire upper surface of the shin bone is called the tibial plateau and, together with the condyles of the thigh bone (femur), forms the knee joint. The articular surface (facies articularis fibularis) for the fibular head (caput fibulae) is found on the lateral circumference of the nearly vertical bone edge.

Tibial resection can be performed using either the extramedullary or intramedullary tibial resection technique. Each of the two techniques offers different setting possibilities for different anatomical conditions and ways of working. Extramedullary means 'located outside the medulla' and refers to the bone marrow (medulla ossium) or spinal cord (medulla spinalis). Intramedullary means 'located within the medulla' and refers to the bone marrow (medulla ossium) or the spinal cord (medulla spinalis).

Many physicians prepare the tibia in two steps in order to perform a check of the prepared bone in between. In a first step, only 2 mm are removed and, for example, in a second step, another 6 mm are removed, so that a total of 8 mm are removed. Some surgeons take the view to always operate in the most bone-sparing way possible and therefore remove as little bone as possible. In this case, a shift in the joint line is intentionally accepted, or compensated for by selecting appropriate implant thicknesses.

Knowledge of the exact thickness of the removed bone part is in any case relevant for the further course of the operation. For this purpose, an orientation apparatus or orientation aid for tibial resection guidance known in the prior art has or consists of a touch apparatus which has a generally helical adjustment element to which a feeler bar with a proximal probe tip is held. Furthermore, a generally helical wheel-shaped setting element is provided, which is in operative engagement with the adjustment element, i.e. the helix, so that the feeler bar can be moved longitudinally to the helix by manual actuation of the helical wheel. Finally, a scale carrier fixed/held on the feeler bar or on the helical wheel and extending longitudinally to the helix is provided with a scale mounted thereon, which indicates a current position of the probe tip along the helix with reference to a marking on the helical wheel or on the helix. If the orientation apparatus constructed in this way is coupled with the saw template, the relative distance between the saw template and the probe tip longitudinally to the helix can be adjusted/fine-tuned.

When determining the thickness of the removed bone part or the bone part to be removed, the setting and reading accuracy of the scale is decisive. In the prior art, however, these two factors are limited. In the prior art, the scale offers stepless graduation in millimeter steps via a thread (operative engagement between helix and helical wheel). During use, however, the surgeon's line of vision is not parallel to the scale but at an angle of approx. 45° from above to a central axis of the stylus/orientation aid. The center axis is the axis around which the helical wheel (setting wheel/rotary knob) of the stylus rotates. In the prior art, this may result in parallax errors (observation errors). In addition, the stepless settability offers room for interpretation as soon as a value is adjusted between two markings. In addition, the height may be adjusted by unintentionally touching the helical wheel/rotary knob, since there is no fixation.

SUMMARY

For this reason, it is necessary and therefore the object of the present invention to provide precise settability of the orientation apparatus and a good readability or detectability of the scale, in particular of the current position of the probe tip on the adjustment element.

The core idea of the present invention is essentially to provide/inform the surgeon with a tactile and/or acoustic signal during use, i.e. during setting/alignment of the orientation aid/touch apparatus according to the invention, from which the surgeon can draw conclusions about the position of the feeler/feeler tip longitudinally to the adjustment element (e.g. helix) or the distance between the feeler and the saw template, without the additional requirement of visually detecting the current scale value (with the eye). Constructively, this can be achieved in that the setting element (e.g. rotary knob/helical wheel) is formed with at least one protrusion and/or recess (first stop part), which can be brought into (latching/stop) contact with a pointer/snapper (second stop part) (fixed with respect to the setting movement of the setting element) in dependence on the (constantly repeating/traversing) setting position in the course of the setting movement of the setting element (e.g. rotation of the helical wheel), whereby the resistance (resistance force) generated by the setting element is changed (increased) against the manually applied setting actuation force. In this way, a surgeon can feel/sense the current relative position (e.g. angle of rotation) between the setting element (e.g. rotary knob) and the pointer/snapper at at least one point in the course of a setting movement of the setting element, and thus infer the position/adjustment travel of the feeler/feeler tip on the adjustment element.

If the first stop part is a cam-shaped projection, the pointer/snapper is elastically pushed (displaced) away from the cam-shaped projection when the setting element is actuated further. As soon as the pointer/snapper has reached the end of the cam-shaped projection when the setting element is correspondingly actuated further, the projection snaps back abruptly (if the projection is shaped correspondingly), which can be heard by a possibly loud clack. In this way, at least one, preferably two (continuously repeating/traversing) setting positions of the setting element can be sensed and/or heard. It should be noted that instead of or in addition to the pointer/snapper mentioned, the cam-shaped projection can also yield elastically.

According to a first aspect of the invention, the orientation apparatus/orientation aid for orienting a saw template has or is a touch apparatus having a feeler whose distance from the saw template is settable, for which the following is provided:
 a movable, preferably rotatable setting means/setting element (e.g. helical wheel or gear wheel),
 an adjustment means/adjustment element with a profiled indentation (e.g. helix or toothed rack), which is in (operative) engagement with the setting means and is also movable by movement/actuation of the setting means,
 a scale carrier having a scale for measuring an adjustment path of the feeler preferably relative to the saw template in the longitudinal direction of the adjustment means,
 at least one first stop means/stop part, which is formed on the setting means,
 at least one second stop means/stop part which is formed on the scale carrier or serving as scale carrier and which is provided and adapted to act as resistance for the first stop means upon movement of the adjustment means by a certain amount of movement or movement distance, wherein
 the second stop means or the first stop means resiliently deflects the respective other stop means upon further movement of the setting means beyond the determined movement amount or movement path.

In a preferred manner, the orientation apparatus according to the invention is a stylus/touch apparatus itself, which is provided and adapted to be coupled or is coupled to a saw template for positioning the saw template on a bone, preferably on a tibial head. The touch apparatus according to the invention may be positioned by an extramedullary or intramedullary holding apparatus or it is part of the holding apparatus.

In a preferred embodiment, the adjustment means moves relative to the setting means. The adjustment means is preferably a cylinder/rod with a thread, in particular an outer thread or helix or a surface with teeth or a cylinder with teeth—i.e. a toothed rack—or a cylinder with profiled indentations or the like.

The setting means is preferably a wheel, in particular a rotary knob or helical wheel in (operative) engagement with the adjustment means or a spring-loaded adjustment head or the like, possibly with a thread, preferably an inner thread, or a toothed wheel or a wheel with teeth or profiled indentations distributed evenly over the circumference or the like. Upon manual actuation, the setting means sets the feeler preferably longitudinally to a longitudinal axis of the adjustment means (helix/rotary knob combination) or perpendicular to an axis of rotation of the setting means (gear rack/gear combination).

According to a preferred embodiment, the feeler, preferably consisting of a feeler bar with a feeler tip arranged proximally thereto and preferably the scale carrier with a scale attached thereto or printed thereon, is firmly connected to the adjustment means or is formed or arranged in one piece so that it can be moved together with the adjustment means. According to an alternative embodiment, it is also possible to hold the feeler movably on the adjustment means and to move this via the setting means for movement of the adjustment means in the longitudinal direction of the adjustment means. The adjustment means thus moves according to a first alternative relative to the setting means or according to a second alternative together with the setting means, wherein the scale or scale carrier (which is preferably fixedly connected to the feeler bar) basically moves relative to the setting means. The scale may thus indicate a relative value or distance at which the feeler is located relative to the setting means.

In concrete terms, the adjustment means may be a hollow cylinder with a helix-like outer thread, which is mounted on an inner shaft that is connected/connectable to the saw template in a rotationally fixed but axially displaceable manner, and the setting means may be a helical wheel with an inner thread that is rotatably mounted (axially fixed) at the free end of the inner shaft, said inner thread being in operative/screw engagement with the outer thread of the hollow cylinder and displacing the hollow cylinder longitudinally to the (inner) axis upon (manual) rotary movement. In this case, the scale/the scale carrier, which is attached to the feeler firmly connected to the hollow cylinder or to the hollow cylinder itself, indicates the sliding path/distance of the hollow cylinder and thus of the feeler to the helical wheel and thus indirectly the distance between the template and the feeler.

The first stop means is preferably formed on the setting means. The first stop means preferably has the form of a groove, a notch or a recess or a projection, a tooth, a spring wire, a spring plate or a nose or the like. One or more of these first stop means may be formed on the setting means, preferably at a certain angular distance from each other, for example 180°. In the case of a wheel/rotating knob as setting means, the at least one stop means co-rotates with each rotation of the wheel. In the case of a spring-loaded adjusting head as setting means, a spring-loaded ball or the like in the head presses against the adjustment means.

The second stop means is formed on the scale or on the scale carrier, or the scale carrier forms the second stop means. The second stop means preferably has the form of a groove, a notch or a recess or a projection, a tooth, a spring wire, a spring plate or a nose or the like. The second stop means is provided and adapted to function as a, preferably latching, resistance to the first stop means. In other words, the second stop means is shaped to come into contact with the first stop means and thereby comes or enters into a latching/latchable engagement therewith.

The first and/or the second stop means are spring mounted or formed on a spring mounting or formed on a spring-elastic component or formed on a spring-elastic scale/scale carrier or forms a spring-elastic component or forms a spring elastic scale. In other words, when the setting element is moved, one (first) stop means comes into contact or engagement with the other (second) stop means. Here, the first and/or the second stop means may be spring-mounted. This means that one stop means presses against the spring-mounting or scale of the other stop means on which it is formed or presses the other stop means itself. One stop means pushes this spring-mounting or scale or the spring-loaded stop means (radially) away from the setting means and the stop means engage in each other or push against each other. When the setting means is moved further, one stop means disengages from the engagement of the other stop means in that the spring-mounting or scale or the other stop means itself is pressed away from the setting means by the one stop means. In this case, the mounting or scale or a stop means itself may be at least one spring element or spring-elastic or have several spring elements in series or parallel, so that when the setting means moves, a stop means always comes back into contact with the other stop means as it travels a predetermined distance. The first and second stop means may be made of any resilient material (e.g. spring steel, plastics or composite materials). The deflection of the stop means may not only be radial to an axis of rotation of the setting means, but also in the direction of rotation around the axis of rotation.

When one stop means engages in the other stop means, the orientation apparatus provides a haptic, tactile, acoustic (a clearly audible click), and/or visible feedback or signal to the user during adjustment. The invention can thus cause the adjustment means to move a predetermined distance when the setting means is rotated, and can cause a signal after this distance. At the same time, the latching function represents the safeguard against accidental setting. Thus, an acoustic and/or tactile feedback is provided for a simple and quick control of the adjusted value and securing of the adjusted value is provided without changing the size of the stylus (probing aid) significantly. Starting from an upper (0 mm) to a lower (12 mm) end stop, the user (e.g. physician or surgeon) can quickly and reliably determine the value to be set based on the number of 'clicks' (engagements), wherein the upper end is in the direction towards the setting means, and the lower end is in the direction towards the saw template or feeler holder. Reading errors can thus be avoided, an increase in safety in use can be ensured and a gain in time with optimum flexibility can be achieved. The field of view onto the bone is not additionally restricted with this solution.

Preferably, the orientation apparatus is configured such that the force required over the entire adjustment range of the scale, i.e. over the entire range in which one stop means engages with the other stop means, is approximately constant, but a stop resistance is generated which can be felt by the doctor/surgeon. This also results in a slim design of the scale.

All embodiments of the invention have the same core idea and may be combined with each other in an analogous manner. Thus, a first stop means of one embodiment may be combined with a stop means of another embodiment to provide acoustic, tactile, and/or visual feedback.

BRIEF DESCRIPTION OF THE DRAWING FIGURES

Figure 5:
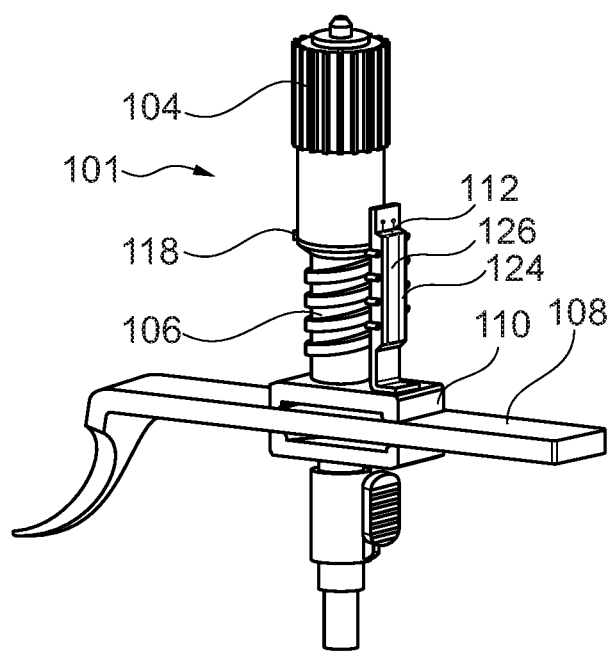
Figure 6:
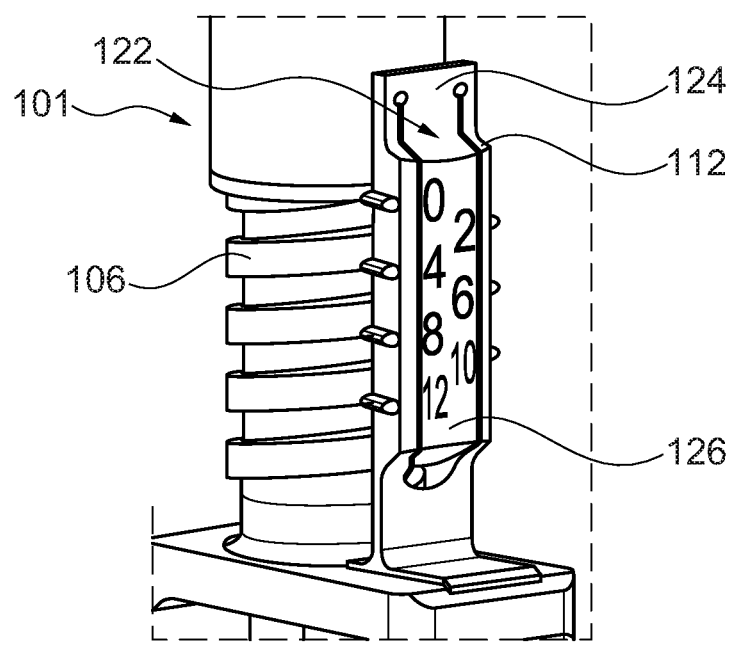
Figure 7:
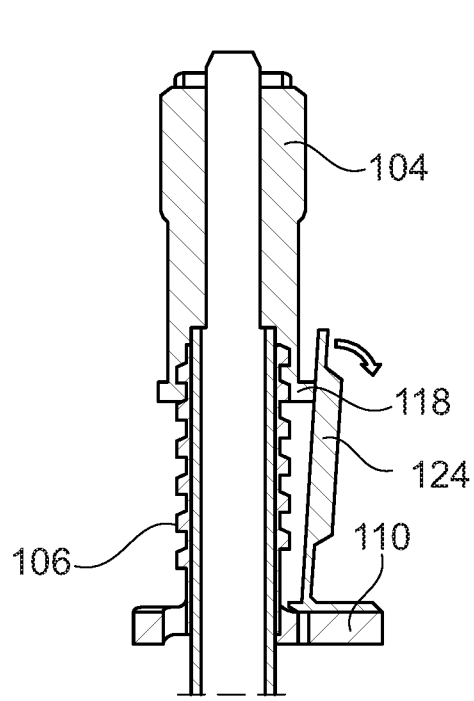
Figure 8:
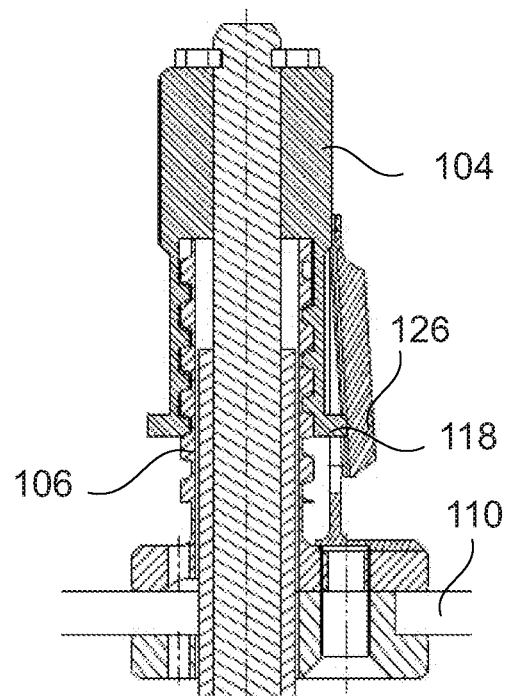
Figure 9:
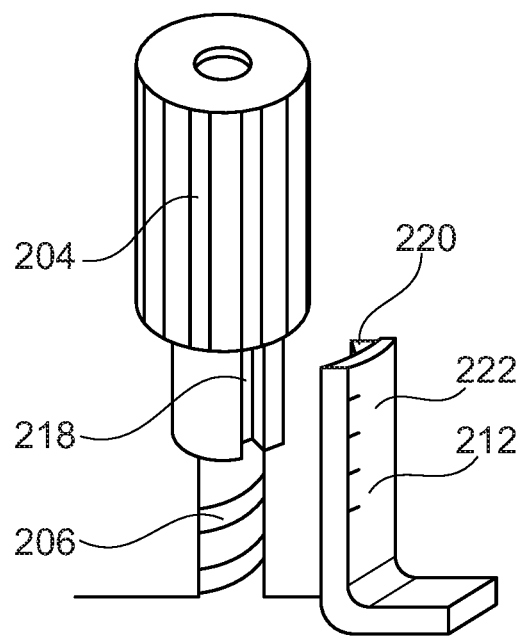
Figure 10:
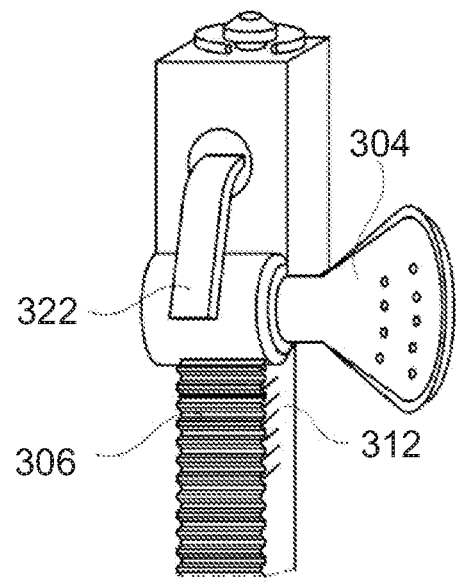
Figure 11:
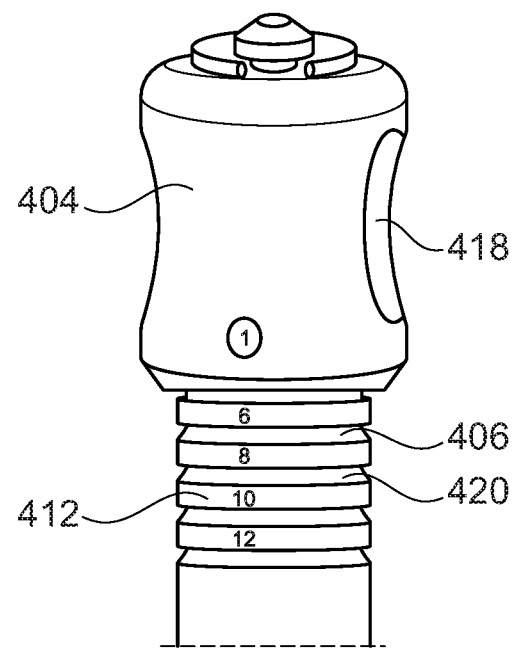
Figure 12:
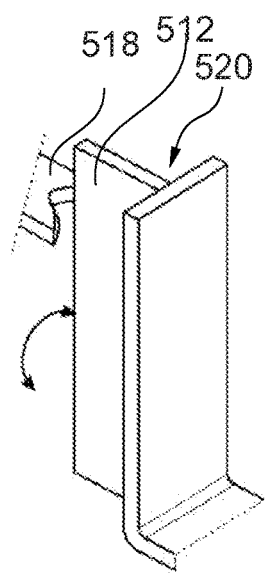
Figure 13:
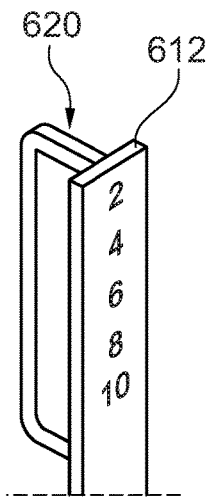
Figure 14:
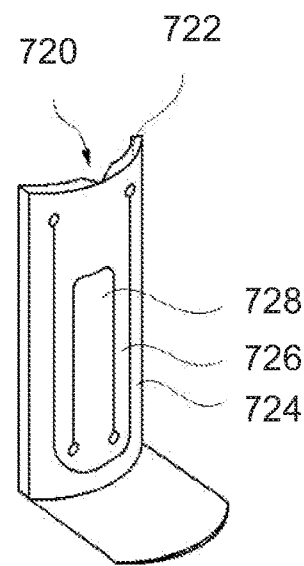
Figure 15:
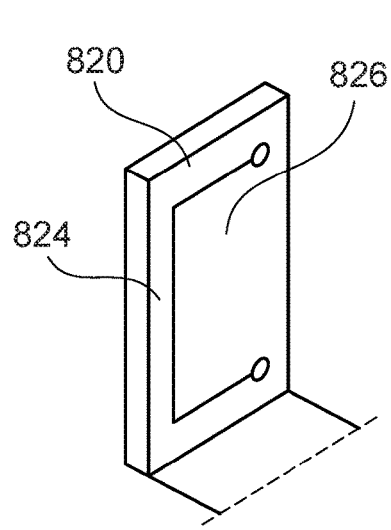
Figure 16:
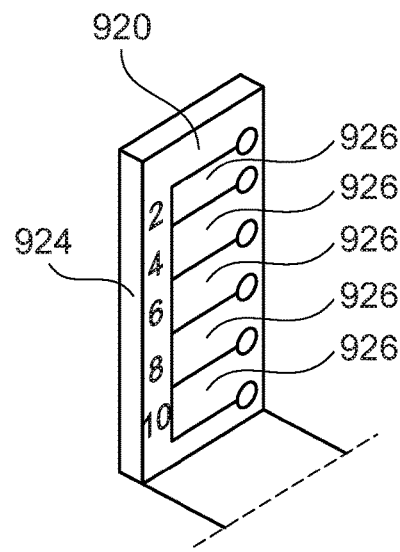
Figure 17:
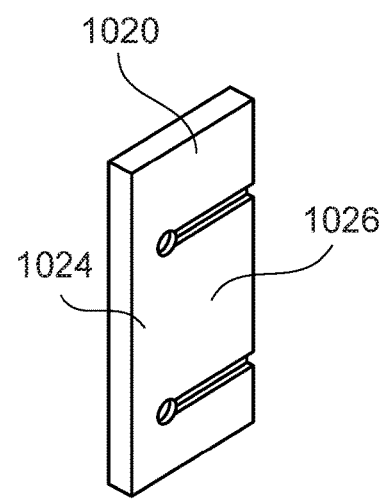
Figure 18:
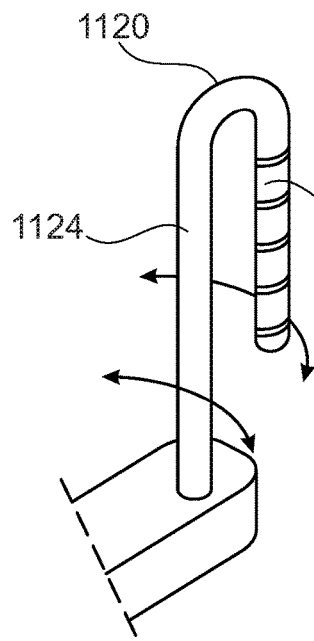
Figure 19:
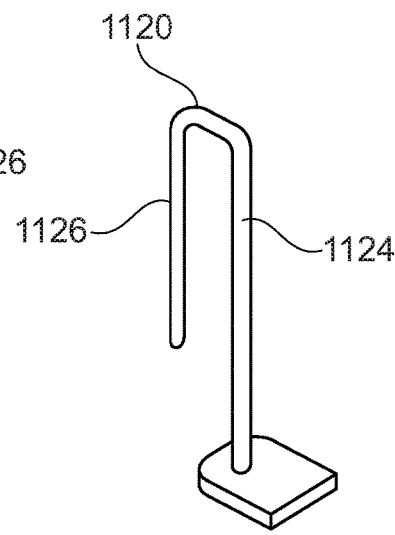
Figure 20:
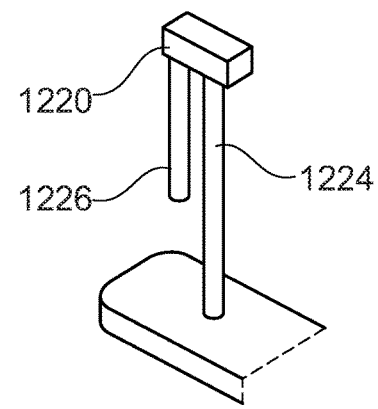
Figure 21:
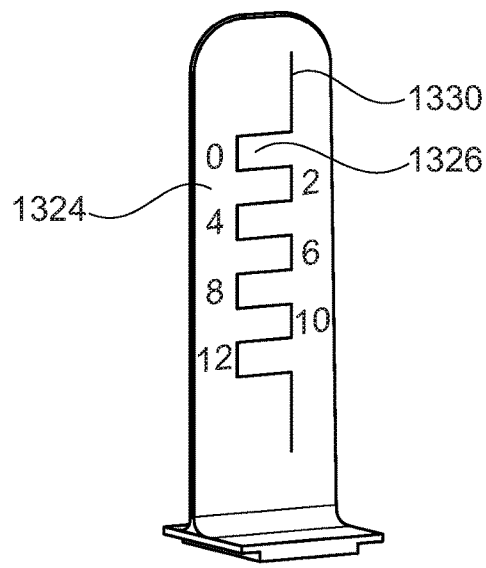
Figure 22:
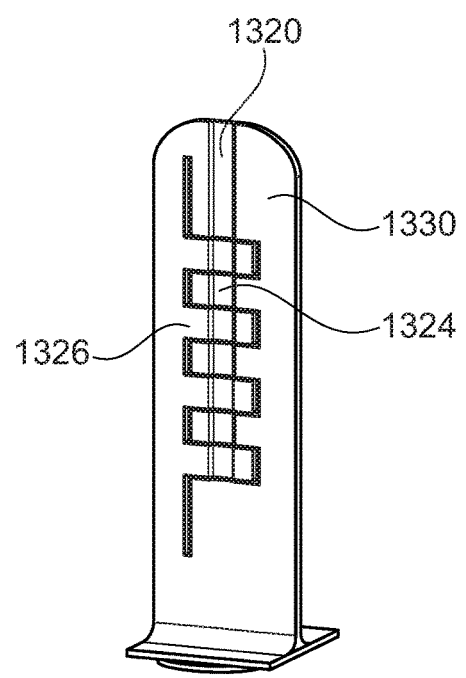
Figure 23:
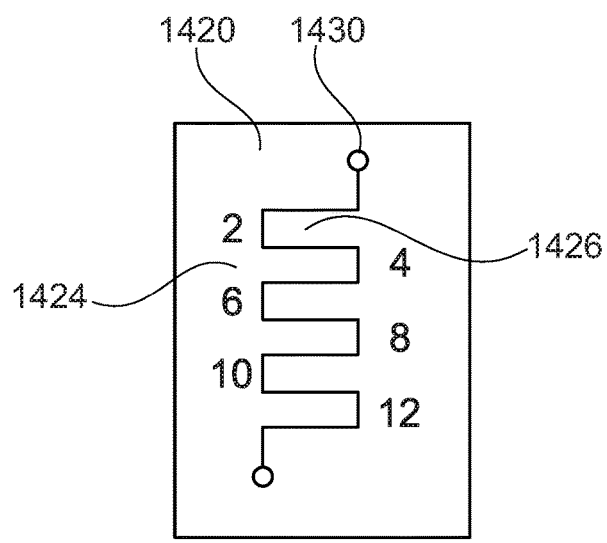
Figure 24:
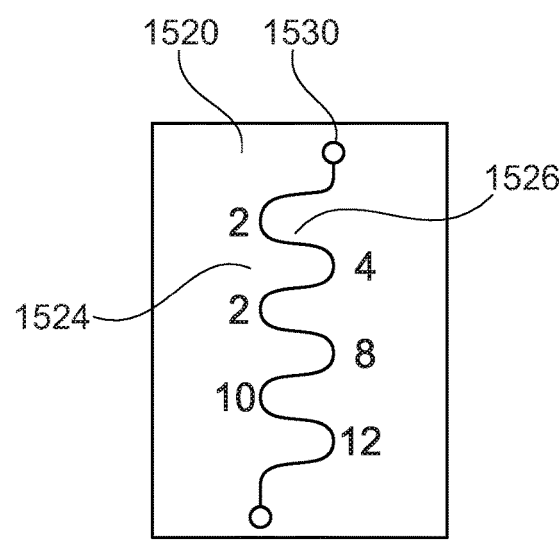
Figure 25:
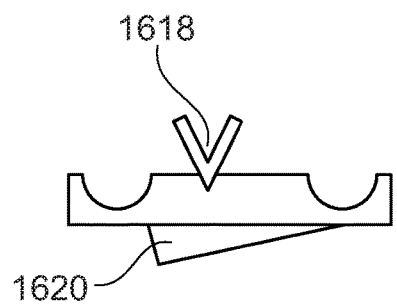
Figure 26:
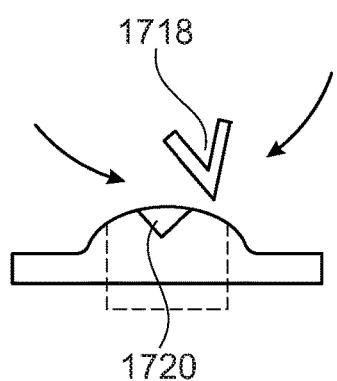

The invention is explained in more detail below based on a preferred embodiment with reference to the accompanying drawings, of which:

FIG. 1 is an orientation apparatus/touch apparatus on an extramedullary framework/holding apparatus, FIG. 2 is an oriented saw template on a tibial head, FIG. 3 is an orientation apparatus/touch apparatus, FIG. 4 is a first embodiment of an orientation apparatus/touch apparatus according to the invention in a rear view, FIG. 5 is the first embodiment of the orientation apparatus according to the invention in a front view, FIG. 6 is the first embodiment of the orientation apparatus according to the invention in a detailed view, FIG. 7 is the first embodiment of the orientation apparatus according to the invention in a cut view in a first position, FIG. 8 is the first embodiment of the orientation apparatus according to the invention in a cut view in a second position, FIG. 9 is a second embodiment of an orientation apparatus/touch apparatus according to the invention, FIG. 10 is a third embodiment of an orientation apparatus/touch apparatus according to the invention, FIG. 11 is a fourth embodiment of an orientation apparatus/touch apparatus according to the invention, FIG. 12 is a fifth embodiment of an orientation apparatus/touch apparatus according to the invention, FIG. 13 is a sixth embodiment of an orientation apparatus/touch apparatus according to the invention, FIG. 14 is a seventh embodiment of an orientation apparatus/touch apparatus according to the invention, FIG. 15 is an eighth embodiment of an orientation apparatus/touch apparatus according to the invention, FIG. 16 is a ninth embodiment of an orientation apparatus/touch apparatus according to the invention, FIG. 17 is a tenth embodiment of an orientation apparatus/touch apparatus according to the invention, FIG. 18 is an eleventh embodiment of an orientation apparatus/touch apparatus according to the invention with lateral load, FIG. 19 is the eleventh embodiment of an orientation apparatus according to the invention with frontal load, FIG. 20 is a twelfth embodiment of an orientation apparatus/touch apparatus according to the invention with frontal load, FIG. 21 is a thirteenth embodiment of an orientation apparatus/touch apparatus according to the invention in front view, FIG. 22 is the thirteenth embodiment of an orientation apparatus/touch apparatus according to the invention in a rear view, FIG. 23 is a fourteenth embodiment of an orientation apparatus according to the invention, FIG. 24 is a fifteenth embodiment of an orientation apparatus/touch apparatus according to the invention, FIG. 25 is a sixteenth embodiment of an orientation apparatus/touch apparatus according to the invention, and FIG. 26 is a seventeenth embodiment of an orientation apparatus/touch apparatus according to the invention.

DETAILED DESCRIPTION

In the following, embodiments of the present disclosure are described based on the corresponding figures.

FIG. 1 shows in principle a possible example of an extramedullary orientation apparatus/holding apparatus for tibial resection guidance, such as may be provided in the present subject matter of the invention. This comprises/has, for example, (not limited thereto) a telescope rod 16, a foot restraint attached to the distal end of the telescope rod 16, a saw template/sawing block 14 fixedly (non-detachably) attached to the proximal end of the telescope rod 16, and a proximal orientation/touch apparatus (stylus) 1 preferably mounted at/on the saw template 14.

The orientation/touch apparatus 1 is used on a tibial head. It usually has a feeler 8, an adjustment means 6 for adjusting a distance between the feeler 8 and the saw template 14, and a setting means 4 for actuating the adjustment means 6.

The setting means 4, for example in the form of a rotary knob, adjusts/actuates, by its manual rotation, the adjustment means 6, for example in the form of a cylinder with outer thread, i.e. a helix. Preferably, the feeler 8 has a proximal feeler tip, which is incorporated/mounted via a feeler bar in/on a feeler holder 10 and is fixedly or (alternatively) movably connected via the latter, i.e. via the outer thread, to the adjustment means 6. This means in both cases that when the setting means 4 is actuated, the feeler holder 10 and thus the feeler 8 moves in the direction towards or away from the setting means 4 corresponding to the actuation amount and the actuation direction. In addition, the feeler 8 is slidably mounted in the feeler holder 10. A scale or scale carrier 12 indicates the distance, or the space, or a relative value of the feeler 8 relative to the setting means 4 in order to correctly position a saw template 14 on the tibial head 2. In other words, the distance of the setting means 4 to the saw template 14 when mounted is known and fixed. Thus, the current distance of the feeler 8 to the saw template 14 can be displayed via the scale 12 located between the setting means 4 and the feeler 8.

FIG. 2 shows the oriented saw template 14 on a tibial head 2, wherein in this case the orientation/touch apparatus is not yet mounted on the saw template.

FIG. 3 shows another view of the orientation/touch apparatus 1 without a saw template. The rotary knob 4, which is mounted on an inner retaining bolt/axis in a rotatable and axially fixed manner, moves the adjustment means 6, i.e. the (hollow) cylinder with the outer thread (helix) 6, the (hollow) cylinder being pushed on the inner retaining bolt in an axially displaceable manner, on which the feeler 8 is held/fixed via a feeler holder 10, in the axial direction, whereby the feeler holder 10 is also moved in the axial direction longitudinally to the inner retaining bolt. The scale/scale carrier 12 is fixedly connected to the feeler holder or the hollow cylinder 6. The rotary knob 4 thus pulls or pushes the hollow cylinder (with outer thread) 6 upwards (towards the proximal direction) towards the rotary knob 4 or pushes it downwards (towards the distal direction) away from the rotary knob 4. In order to be able to better grip the rotary knob 4, it has an axial portion with an outer knurl/riffle or outer grip surface, as shown in particular in FIG. 3.

FIG. 4 specifically shows a first embodiment of an orientation apparatus 101 according to the invention in a rear view, which is based on the orientation apparatus 1 described above in principle. The orientation apparatus 101 has the setting means 104 in the form of the rotary knob, which is axially fixed and rotatably mounted around the inner (rotationally fixed) retaining bolt and which, by rotation on the retaining bolts, adjusts the height of the adjustment means 106 in the form of the (hollow) cylinder with an outer thread (helix) longitudinally to the retaining bolt. The feeler 108 is firmly coupled/connected to the adjustment means 106 via the feeler holder 110. In this case, the scale or scale carrier 112 is attached to the feeler holder 110, projects in the direction of the setting means 104 and thus indicates the height/distance of the feeler 108 relative to the setting means 104 in order to position the saw template (not shown in FIG. 4) correctly on a tibial head. The feeler 108 in the feeler holder 110 on the adjustment means 106 and the scale 112 on/at the feeler holder 110 thus move relative to the setting means 104 upon rotation/actuation of the setting means (rotary knob) 104. In this respect, the structure of the invention is analogous to the orientation apparatus of the preceding figures.

The setting means 104 of the invention also has the axial portion with a roughened/riffled outer surface, which is followed, in accordance with the invention, distally (in the direction towards the feeler holder) by an axial portion with a comparatively smooth outer surface, which is provided and configured to be overlapped by the scale carrier 112 radially on the outside in the axial direction (see in particular FIG. 4). The setting means 104 has, in particular in the axial portion with smooth outer surface, a first stop means 118, for example in the form of a projection, which rotates together with the setting means (rotary knob) 104. When the setting means 104 is rotated to a certain rotational position, the projection 118 contacts/abuts on the scale, or the scale carrier 112, which is spring-elastic in the invention according to this embodiment. The projection 118 thus presses against the scale/scale carrier 112 during (further) rotation, which thus (radially) elastically moves away from the center axis/rotation axis of the setting means 104, i.e. is displaced radially outwards, whereby (with displacement of the scale carrier 112 radially outwards) an increased resistance to rotation is generated. In the scale/scale carrier 112, on the side facing the setting means 104 and thus also the projection 118, a further stop means 120 is inserted or formed, for example in the form of a groove, which extends parallel to the axis of rotation. The projection 118 thus engages (abruptly) in the groove 120 when the setting means 104 is rotated further, and the scale/scale carrier 112 thus moves quickly or abruptly in the direction of the projection 118 (i.e. radially inwards) as a result of the spring pressure, whereby an acoustic, tactile, haptic and/or partly also visible feedback or signal (latching click) is given to the user.

For example, a single rotation of the setting means 104 causes the feeler 108 to move one or two millimeters relative to the setting means 104 longitudinally to the adjustment means 106, wherein after each rotation (corresponding to each millimeter or two millimeters) the first stop means 118 engages the further (second) stop means 120, thereby providing feedback to the user so that the user knows that the feeler 108 has been moved one or two millimeters by a corresponding rotation of the setting means 104.

As already explained above, it is preferred to firmly connect the feeler holder 110 to the adjustment means 106. In this case, the inner axis/retaining bolt is provided (see in particular FIG. 8), onto which the adjustment means 106 in the form of the hollow cylinder with the outer thread is axially displaceable and preferably fixed against rotation. The setting means 104 in the form of the previously described rotary/helical wheel is mounted in a rotatable but axially fixed manner at the proximal free end/end portion of the (inner) axis and has an inner thread that is in screw engagement with the outer thread of the adjustment means 106. As the setting means 104 is rotated about the (inner) axis, the adjustment means 106 in the form of the hollow cylinder is moved axially, longitudinally to the (inner) axis/retaining bolt, thus changing the distance between the feeler 108 and the setting means 104. Alternatively, it would also be conceivable to connect the rotary knob firmly to the adjustment means (helix) 106 and to rotate the adjustment means 106 when the setting means 104 is actuated. In this case, the feeler holder 110 is in screw engagement with the outer thread of the adjustment means 106 and is axially displaced when the adjustment means is rotated accordingly. As an anti-rotation device for the feeler holder 110, the feeler 108 could, for example, be held manually or could be guided longitudinally in a stationary rail (not shown) arranged parallel to the adjustment means 106.

FIG. 5 shows a front view of the first embodiment of the orientation apparatus 101 according to the invention. The structure is analogous to FIG. 4. The setting means 104 moves the feeler holder 110 via the adjustment means/helix 106 (which is fixedly connected to the feeler holder 110 and/or the scale carrier 112) by rotation around the (inner) retaining bolt, whereby the feeler 108 in the feeler holder 110 is also moved. The scale 112 is preferably attached to the feeler holder 110 and is thus firmly connected to the feeler holder 110. The first stop means 118 on the setting means 104 comes into contact with the scale/scale carrier 112 and bends it outwards, i.e. away from the axis of rotation. Since the scale/scale carrier 112 is attached at its lower (distal) end to the feeler holder 110, the force required to bend the scale 112 outwards is lower at the top (proximally) than at the bottom (distally) where the scale is attached (due to leverage). This means that less force is required at the top (proximally) to deflect the scale 112 than further down (distally). Preferably, the scale/scale carrier 112 is made of spring steel or another metal with a high spring stiffness or spring elasticity. However, the scale/scale carrier 112 according to the invention is preferably divided into two serial spring elements 124 and 126 which divide the force in series (see FIG. 7 and FIG. 8). The scale/scale carrier 112 preferably has the shape of a platelet/rectangle, which is firmly connected to the feeler holder 110 at one end. An incision is made in the scale/scale carrier 112 in the form of an inverted U, whereby the first spring element 124 is formed by the outer scale frame created thereby and the second spring element 126 is formed by the inner spring tongue created thereby, wherein the spring tongue is fixed to the scale frame at the axially free end (upper/proximal end) of the scale frame. Due to this series arrangement of the spring elements 124 and 126, the force for pushing away the scale carrier via the first stop at the lower (distal) end of the scale/scale carrier is essentially the same as the force for pushing away the scale carrier via the first stop at the upper (proximal) end of the scale/scale carrier (lever path to the respective pivot point 'down/up' remains essentially the same).

FIG. 6 shows a detailed view of a first embodiment of an orientation apparatus 101 according to the invention. The adjustment means 106 is fixedly connected to the scale 112 via the feeler holder 110. In other words, the scale 112 is a spring 122 with a first bending spring element 124 and a second bending spring element 126 connected in series with the first spring element, wherein the pivot points of the two bending springs are positioned at the opposite ends of the spring. The U-shaped recess in the scale 112 extends the lever of the entire spring 122, wherein the first spring element 124 and the second spring element 126 are in series. Through the recess, the first spring element 124 is formed by two side elements laterally enclosing the U-shaped recess. In order to obtain the desired latching effect and an acoustic feedback (a clearly audible click), the scale 112 is constructed resiliently in the upper and lower area, namely in the upper area by the (outer, frame-shaped) spring element 124, in the lower area by the (inner, tongue-shaped) spring element 126. The tongue-shaped spring element 126 thus avoids a (linearly) increasing force when the rotary knob/setting means 104 is turned downwards, or when the setting means 104 pulls the adjustment means 106 upwards. The second (tongue-shaped) spring element 126 has the fixed point at the upper/proximal end of the scale 112, wherein upper refers to the non-fixed side of the scale 112 at the feeler holder 110, and the first (frame-shaped) spring element 124 has the fixed point at the lower/distal side to the feeler holder 110. Accordingly, the frame 124 works as a spring in the upper area. The further the adjustment means 106 is moved towards the setting means 104, the more the inner tongue or the spring element 126 takes over the spring function. The acoustic feedback occurs when the first stop means 118 engages the second stop means 120, which is located in one of the two spring elements 124 or 126, e.g. per revolution at 2 mm thread pitch.

FIG. 7 shows the first embodiment of the orientation apparatus 101 according to the invention in a cut view in a first position. The first position shows the setting means 104 which embraces the adjustment means 106 and is able to move the adjustment means 106 by rotation of the setting means 104. The setting means 104 has two projections 118, wherein one of the projections presses against the first spring element 124, which is attached at one end to the feeler holder 110. The projection 118 forces the spring element away from the setting means 104, causing the spring element to deflect radially outwards.

FIG. 8 shows the first embodiment of the orientation apparatus 101 according to the invention in a cut view in a second position. In the second position, the setting means 104 has pulled the adjustment means 106 towards it, whereby the feeler holder 110 with the scale thereon is also closer to the setting means 104. The projection 118 is now close to the feeler holder 110. The U-shaped recess now pushes the second spring element 126 outwards and away from the setting means 106.

FIG. 9 shows a second embodiment of an orientation apparatus according to the invention. In this embodiment, the setting means 204 is rotatably mounted on the adjustment means 206 and moves the latter, in a manner as described above. In this embodiment, the first stop means 218 on the setting means 206 is a groove extending externally of the setting means 204 parallel to the axis of rotation of the setting means 204. At the scale 212, which is a spring 222 analogous to the first embodiment and has a spring elasticity, the second stop means 220 is in the form of a projection.

FIG. 10 shows a third embodiment of an orientation apparatus according to the invention. A setting means 304 is configured in the form of a gear that engages the adjustment means 306 in the form of a surface with teeth. A scale is formed on the side of the adjustment means 306. A spring 322 has a projection on a side facing the setting means 304 (not shown) that engages the teeth of the setting means 304 and thus provides acoustic and haptic feedback to the user when the user rotates the setting means 304.

FIG. 11 shows a fourth embodiment of an orientation apparatus according to the invention. The setting means 404 has a spring-preloaded ball (not shown) in an inner side as a first stop means 418. The adjustment means 406 has indentations that serve as a second stop means 420. A scale 412 is applied to the adjustment means at the projections between the indentations.

FIG. 12 shows a fifth embodiment of an orientation apparatus according to the invention. A scale 512 is formed with a T-shaped cross-section. In other words, a rectangular surface at its long central axis has another rectangular surface perpendicular thereto. This second surface or flag is a spring-elastic stop means 520 in the form of a spring plate which engages or can latch into a second stop means 518 (e.g. a groove) on a setting means (not shown).

FIG. 13 shows a sixth embodiment of an orientation apparatus according to the invention. A scale 612 is formed with a wire as a stop means 520. In other words, a rectangular surface has on its long central axis an angled, spring-elastic wire/spring wire thereto, which is connected at two ends to the scale 612. This wire is thus a spring-elastic stop means 620 which engages or can latch into a second stop means (e.g. a groove) on a setting means (not shown).

FIG. 14 shows a seventh embodiment of an orientation apparatus according to the invention. The scale or spring 722 is analogous to the first embodiment with the exception that the scale has a third spring element 728 in series with a first spring element 724 and a second spring element 726. The third spring element 726 is again in the form of a U, that is offset by exactly 180° from the first U, and has its fixed point again at the upper end. This means that the force required is even more linear than in the first embodiment.

FIG. 15 shows an eighth embodiment of an orientation apparatus according to the invention. Here, the second stop means 820 is similar to the first embodiment, with the difference that the second spring element 826 is mounted in the first spring element 824 in a U-shape rotated at an angle of 90°, or has the fixed point at an angle of 90° to the lower end.

FIG. 16 shows a ninth embodiment of an orientation apparatus according to the invention. In this embodiment, the second stop means 920 is provided with a plurality of second spring elements 926, which are formed as in the eighth embodiment. The plurality of second spring elements 926 are arranged in parallel from bottom to top and are framed by the first spring element 924.

FIG. 17 shows a tenth embodiment of an orientation apparatus according to the invention. In this embodiment, the second stop means 1020 has at least two incisions that run parallel to the lower end of the stop means 1020 where it is attached to the feeler holder (not shown). Thus, the stop means 1020, which also forms the scale, is radially deflected at different locations.

FIG. 18 shows an eleventh embodiment of an orientation apparatus according to the invention with lateral load. The stop means 1120 comprises a spring wire in the form of a hook/U attached at one end to the feeler holder. A first spring element 1124 has the fixed point at the feeler holder, a second spring element 1126 has the fixed point at the upper end of the first spring element 1124. As shown by the arrows, the stop means 1120 can be deflected in the direction of rotation of a rotatable setting means (not shown).

FIG. 19 shows the eleventh embodiment of an orientation apparatus according to the invention with frontal load. In addition to the rotational deflection of the first spring element 124 and/or second spring element 126 shown in FIG. 18, the second stop means 1120 may also undergo a radial orientation as shown by the arrows in FIG. 19.

FIG. 20 shows a twelfth embodiment of an orientation apparatus according to the invention with frontal load. The structure of the twelfth embodiment is analogous to the eleventh embodiment, except that the stop means 1220 does not consist of a single U-shaped wire, but that the first spring element 1224, in the form of a straight spring wire, is connected at its upper end by a plate or the like to the second spring element 1226, which is formed parallel to the first spring element 1224 in the form of a straight spring wire.

FIG. 21 shows a thirteenth embodiment of an orientation apparatus according to the invention in front view. In this embodiment, the scale has a rectangular cut 1330. The rectangular cut 1330 leads from the vicinity of the upper end of the scale to the vicinity of the lower end of the scale. The scale is divided by the rectangular cut 1330 into a first spring element 1324 and a second spring element 1326. This embodiment allows for audible, visual, and tactile feedback according to the principle of a barrel organ. When one rectangular surface is deflected by a projection of a setting means (not shown), the other spring element springs back and vice versa.

FIG. 22 shows the thirteenth embodiment of an orientation apparatus according to the invention in a rear view. At the rear of the scale, a groove 1320 is provided as a second stop means extending from the upper end to the lower end and passing through the first spring element 1324 and the second spring element 1326. The groove also extends through the rectangular cut.

FIG. 23 shows a fourteenth embodiment of an orientation apparatus according to the invention. This embodiment is analogous to the thirteenth embodiment with the only difference that this embodiment does not have a groove on the rear side and serves as a second stop means 1420 without a groove. Likewise, in this embodiment, a rectangular cut 1430 separates the stop means into a first spring element 1424 and a second spring element 1426 from top to bottom.

FIG. 24 shows a fifteenth embodiment of an orientation apparatus according to the invention. This embodiment is analogous to the thirteenth or fourteenth embodiment with the difference that a cut 1530 is not rectangular but has the shape of a wave and a second stop means 1520 is divided into a first spring element 1524 and a second spring element 1526.

FIG. 25 shows a sixteenth embodiment of an orientation apparatus according to the invention. This embodiment is applicable to any of the preceding embodiments having a further spring element/second spring element separated from the first spring element by a U-shaped cut in the scale. Here, a first stop means 1618 is brought to a second stop means 1620 by rotation of a setting means. The second stop means 1620 moves radially away from an axis of rotation of the rotatable setting means. The first stop means 1618 abuts a frame of the second stop means 1620. The second stop means 1620 is separated from the rest of the scale by a cut, preferably a U-shaped cut, so that it can be deflected on one side.

FIG. 26 shows a seventeenth embodiment of an orientation apparatus according to the invention. This embodiment is applicable to any of the preceding embodiments having a further spring element/second spring element separated from the first spring element by a U-shaped cut in the scale. In this embodiment, the second stop means 1720 has a rounded surface around a groove so that the first stop means 1718 comes into more gentle contact therewith.

In summary, the present invention relates to a touch/orientation apparatus comprising, for orienting a saw template, a setting means, an adjustment means having a profiled indentation and a feeler movable relative to the setting means, a scale for measuring a height of the setting means relative to the adjustment means, at least one first stop means formed on the setting means, at least one second stop means formed on the scale or serving as a scale and provided and adapted to act as a resistance for the first stop means, wherein the second stop means and/or the first stop means resiliently deflects the respective other stop means.

The invention claimed is:

1. An orientation aid for tibial resection guidance having or consisting of a touch apparatus comprising: a helical-shaped or rack-shaped adjustment element; a feeler held on the helical-shaped or rack-shaped adjustment element; a helical wheel-shaped or toothed wheel-shaped setting element which is in engagement with or coupled to the helical-shaped or rack-shaped adjustment element in order to move the feeler via the helical-shaped or rack-shaped adjustment element by manual operation of the helical wheel-shaped or toothed wheel-shaped setting element; a scale carrier coupled to the feeler or to the helical-shaped or rack-shaped adjustment element and extending longitudinally to the helical-shaped or rack-shaped adjustment element, wherein the scale carrier indicates a current position of the feeler, with reference to a marking on the helical wheel-shaped or toothed wheel-shaped setting element, on the feeler, or on the helical-shaped or rack-shaped adjustment element; a first latch part or stop part; and a second latch part or stop part, the first latch part or stop part and/or the second latch part or stop part being spring-elastically flexible or mounted in a spring-elastically flexible manner, so that the first latch part or stop part, resiliently deflects the second latch part or stop part upon actuation of the helical wheel-shaped or toothed wheel-shaped setting element in a specific relative rotational position or within a specific relative position range between the scale carrier and the helical wheel-shaped or toothed wheel-shaped setting element and, upon further actuation of the helical wheel-shaped or toothed wheel-shaped setting element, the second latch part or stop part springs back, into a latching or stop engagement with the first latch part or stop part, the first latch part or stop part being formed on the helical wheel-shaped or toothed wheel-shaped setting element, and the second latch part or stop part being formed on or formed by the scale carrier.

2. The orientation aid according to claim 1, wherein the second latch part or stop part engages the first latch part or stop part when the second latch part or stop part springs back into the latching or stop engagement with the first latch part or stop part and generates a haptic, tactile, acoustic and/or visible feedback or signal.

3. The orientation aid according to claim 1, wherein the helical-shaped or rack-shaped adjustment element has or is an outer thread.

4. The orientation aid according to claim 1, wherein the helical wheel-shaped or toothed wheel-shaped setting element is a rotary knob.

5. The orientation aid according to claim 1, wherein the first latch part or stop part is one of a groove and a projection, and the second latch part or stop part is the other of the groove and the projection.

6. The orientation aid according to claim 1, wherein the scale carrier is formed integrally with the feeler or is formed as a single component and is mounted at the feeler.

7. The orientation aid according to claim 1, wherein the scale carrier comprises a first spring element and a second spring element in series, the first spring element being coupled at its distal end to the feeler and extending towards a proximal direction, and the second spring element being connected to a proximal end or end portion of the first spring element and extending towards a distal direction.

8. The orientation aid according to claim 1, further comprising a retaining bolt provided and configured to be connected at its distal end portion to a saw template, the retaining bolt serving as a rotationally fixed axial sliding guide for the helical-shaped or rack-shaped adjustment element formed as a hollow cylinder with an outer thread, and, at its free, proximal end portion, supports, in a rotatable and axially fixed manner, the helical wheel-shaped or toothed wheel-shaped setting element in the form of a helical wheel with an inner thread, which is in screwed engagement with the outer thread of the hollow cylinder in order to move, upon rotary actuation, the hollow cylinder longitudinally to the retaining bolt.

9. The orientation aid according to claim 8, wherein the helical wheel has a proximal actuation portion and a distal axial portion overlapped at its radially outer side by the scale carrier over an axial path, wherein the axial path varies depending on an amount of actuation of the helical wheel.

10. The orientation aid according to claim 9, wherein the first latch part or stop part is formed in the distal axial portion.

* * * * *